(12) United States Patent
Osawa et al.

(10) Patent No.: US 7,256,890 B2
(45) Date of Patent: Aug. 14, 2007

(54) SPECTROSCOPE AND MICROSPECTROSCOPE EQUIPPED THEREWITH

(75) Inventors: Hisao Osawa, Kashiwa (JP); Naoshi Aikawa, Fujisawa (JP); Akira Adachi, Sagamihara (JP)

(73) Assignee: Nikon Corporation, Tokyo (JP)

( * ) Notice: Subject to any disclaimer, the term of this patent is extended or adjusted under 35 U.S.C. 154(b) by 81 days.

(21) Appl. No.: 11/281,536

(22) Filed: Nov. 18, 2005

(65) Prior Publication Data

US 2006/0114458 A1    Jun. 1, 2006

(30) Foreign Application Priority Data

Nov. 26, 2004    (JP) ............................. 2004-342718

(51) Int. Cl.
*G01J 3/28* (2006.01)
*G01J 3/447* (2006.01)

(52) U.S. Cl. .................. 356/328; 356/326; 356/327

(58) Field of Classification Search ................ 356/328, 356/326, 331, 334, 344, 305–309; 385/15, 385/24; 359/629
See application file for complete search history.

(56) References Cited

U.S. PATENT DOCUMENTS

| | | | |
|---|---|---|---|
| 5,886,785 A | * | 3/1999 | Lefevre et al. ............. 356/328 |
| 6,498,872 B2 | | 12/2002 | Bouevitch et al. ............ 385/24 |
| 6,753,960 B1 | * | 6/2004 | Polynkin et al. ............ 356/330 |
| 2002/0126385 A1 | * | 9/2002 | Asami et al. ................ 359/571 |
| 2002/0131691 A1 | * | 9/2002 | Garrett et al. ................. 385/24 |
| 2002/0181858 A1 | * | 12/2002 | Bouevitch ..................... 385/24 |
| 2005/0157397 A1 | * | 7/2005 | Efimov et al. .............. 359/629 |

FOREIGN PATENT DOCUMENTS

JP    05127097 A    *    5/1993

* cited by examiner

*Primary Examiner*—Tarifur Chowdhury
*Assistant Examiner*—Daniel Cartoon
(74) *Attorney, Agent, or Firm*—Miles & Stockbridge P.C.

(57) ABSTRACT

A spectroscope capable of suppressing the dimension and the cost with avoiding a problem caused by polarization dependency of the diffraction grating. The spectroscope includes a polarizing beam splitter plate 3 that divides the light from an input fiber 1 into a first and a second optical paths and polarizes each light of each optical path having different direction of polarization with each other, a Fresnel rhomb half wave plate 5 that arranges the direction of polarization of the light in the first optical path into that in the second optical path and a plane mirror 4 that deflects the second optical path such that at least a portion of an area where the light through the first optical path is incident on the diffraction grating 6 and an area where the light through the second optical path is incident on the diffraction grating overlap each other.

15 Claims, 5 Drawing Sheets

SPECTROSCOPE AND MICROSPECTROSCOPE EQUIPPED THEREWITH

The disclosures of the following priority application is herein incorporated by reference:

Japanese Patent Application No. 2004-342718 filed on Nov. 26, 2004.

BACKGROUND OF THE INVENTION

1. Field of the Invention

The present invention relates to a spectroscope equipped with a spectroscopic element for dispersing input light from an input portion and a microspectroscope equipped therewith.

2. Related Background Art

A diffraction grating has been widely used as a spectroscopic element for a spectroscope. The diffraction grating has polarization dependency, so that diffraction efficiency thereof is generally considered to be higher in S-polarized light that the direction of electric field oscillation thereof is perpendicular to the direction of grooves of the diffraction grating than in P-polarized light that the direction of electric field oscillation thereof is parallel to the direction of grooves of the diffraction grating. In particular the long wavelength range where the wavelength of the incident light is comparable or longer than the period (a pitch of the grooves) of the diffraction grating, the tendency becomes conspicuous. In other words, the shorter the period of the diffraction grating becomes, the more conspicuous the tendency appears, so that when a diffraction grating with high resolution is used, it should be noted.

Accordingly, in order to solve the difference in diffraction efficiency according to direction of polarization, a technique is disclosed in U.S. Pat. No. 6,498,872 B2.

The technique is to arrange the direction of polarization of the incident light into the diffraction grating. In particular, the light coming out from an incident port is divided into P-polarized light and S-polarized light by a polarizing beam splitter, the P-polarized light is converted into S-polarized light by half wave plate, and the S-polarized light beam and the S-polarized light beam converted from the P-polarized light are led to a diffraction grating parallel with each other.

In the technique disclosed in U.S. Pat. No. 6,498,872 B2, since the directions of polarization of the incident light into the diffraction grating are arranged, the problem according to polarization dependency of the diffraction grating is solved. However, since the S-polarized light and the S-polarized light converted from the P-polarized light are incident to the diffraction grating on respective areas different with each other, the diffraction grating becomes large resulting in a problem that the instrument becomes large and costly.

SUMMARY OF THE INVENTION

The present invention is made in view of the aforementioned problems and has an object to provide a spectroscope capable of suppressing the dimension and the cost with avoiding a problem caused by polarization dependency of the diffraction grating and a microspectroscope equipped therewith.

According to a first aspect of the present invention, there is provided a spectroscope including, an input portion, a spectroscopic element that disperses light come out from the input portion, an exit portion that exits the light dispersed by the spectroscopic element, or a detector that detects the light dispersed by the spectroscopic element, a polarization dividing element that divides the light from the input portion into a first optical path and a second optical path and gives each light of each optical path different direction of polarization with each other, a polarization rotator that is disposed in the first optical path and arranges the direction of polarization of the light in the first optical path into the direction of polarization of the light in the second optical path, and a beam deflector that is disposed in either one optical path of the first optical path and the second optical path and deflects the one optical path such that at least a portion of an area where the light proceeding through the one optical path is incident on the spectroscopic element and an area where the light proceeding through the other optical path is incident on the spectroscopic element overlap each other.

In the spectroscope according to the first aspect of the present invention, it is preferable that the polarization dividing element is a polarizing beam splitter plate having a plane parallel plate shape.

In the spectroscope according to the first aspect of the present invention, it is preferable that the polarization dividing element is a polarizing beam splitter cube having an incident surface and an exit surface and the incident surface of the polarizing beam splitter cube is inclined with respect to the exit surface.

In the spectroscope according to the first aspect of the present invention, it is preferable that the incident surface of the polarizing beam splitter cube is not perpendicular to the incident light.

In the spectroscope according to the first aspect of the present invention, it is preferable that the polarization rotator is a Fresnel rhomb half wave plate.

In the spectroscope according to the first aspect of the present invention, it is preferable that the spectroscope further includes a superposition optical element that superposes at least a portion of an area where the light proceeding through the other optical path and being dispersed by the spectroscopic element is incident on the exit portion or the detector relative to an area where the light proceeding through the one optical path and being dispersed by the spectroscopic element is incident on the exit portion or the detector.

In the spectroscope according to the first aspect of the present invention, it is preferable that the spectroscopic element is a diffraction grating on which a plurality of grooves are formed parallel with each other and an incident angle of the light proceeding through the one optical path incident on the diffraction grating and an incident angle of the light proceeding through the other optical path incident on the diffraction grating are substantially the same angle in a plane perpendicular to the direction of the groove and different in a plane including the groove.

In the spectroscope according to the first aspect of the present invention, it is preferable that the incident angle of the light proceeding through the one optical path incident on the diffraction grating and the incident angle of the light proceeding through the other optical path incident on the diffraction grating have the same absolute value.

According to the second aspect of the present invention, there is provided a microspectroscope including, a confocal microscope and the spectroscope according to the first aspect of the present invention. The confocal microscope includes a laser light source, a converging optical system that converges the light from the laser light source onto an observing surface, a pinhole member on which a pinhole, which is optically conjugate with the observing surface, is formed, and an optical system capable of converging the light reflected from the observing surface onto the pinhole. The spectroscope disperses the light passing through the pinhole of the confocal microscope.

Other features and advantages according to the invention will be readily understood from the detailed description of the preferred embodiment in conjunction with the accompanying drawings.

BRIEF DESCRIPTION OF THE DRAWINGS

FIGS. 2A, 2B, and 2C are graphs showing the spectroscope according to an embodiment of the present invention in which

DESCRIPTION OF THE MOST PREFERRED EMBODIMENTS

Embodiments according to the present invention are explained below with reference to accompanying drawings.

Figure 1:
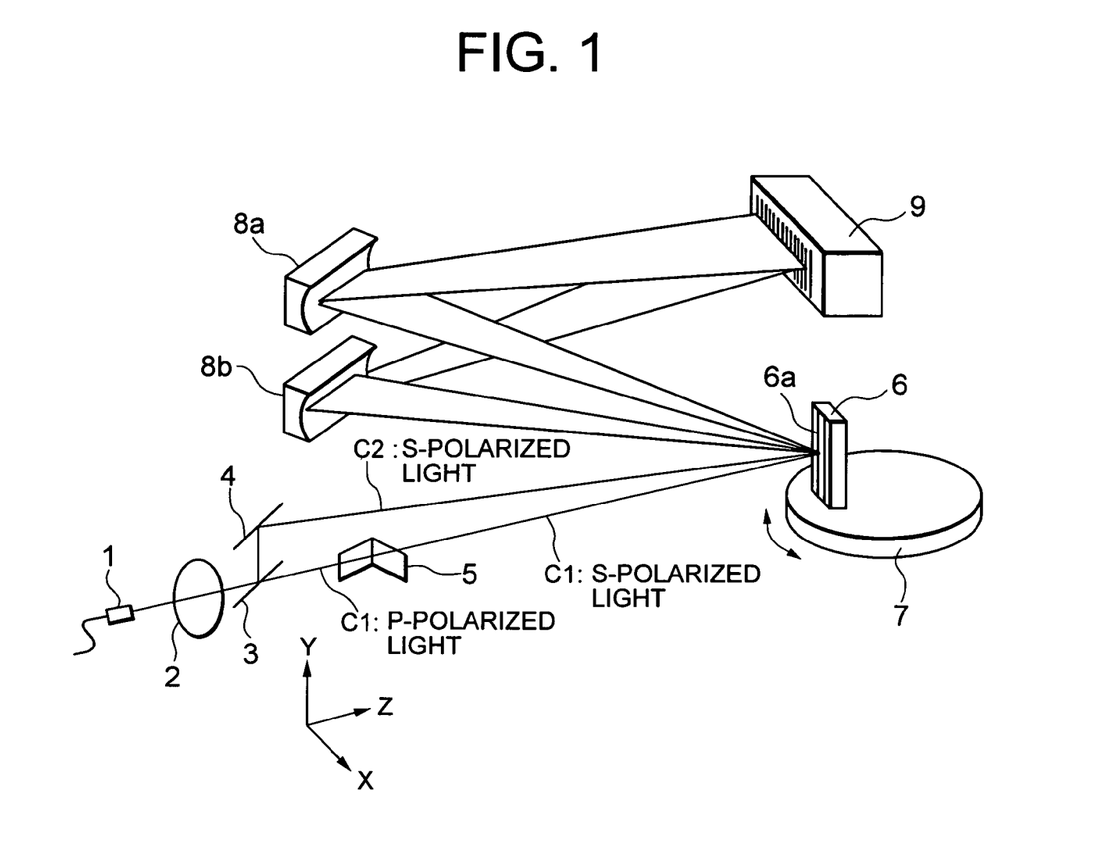
FIG. 1 is a perspective view showing a spectroscope according to an embodiment of the present invention.

As shown in FIG. 1, a spectroscope according to an embodiment of the present invention includes an input fiber 1, a collimator lens 2 for collimating the light from the input fiber 1, a polarizing beam splitter plate 3 for dividing the collimated light into a first optical path C1 and a second optical path C2 and giving respective light beams along the first optical path C1 and the second optical path C2 different directions of polarization with each other, a reflecting type diffraction grating 6 for dispersing the light passing through the first optical path C1 and that through the second optical path C2, a diffraction grating table 7 having a rotational axis parallel to the direction of the grooves 6a of the diffraction grating 6, a Fresnel rhomb type half wave plate 5 for arranging the direction of polarization of the light along the first optical path C1 to that along the second optical path C2, a plane mirror 4 for deflecting the second optical path C2 such that an incident area where the light passing through the second optical path C2 is incident and an incident area where the light passing through the first optical path C1 is incident overlap each other on the diffraction grating 6, a photodetector array 9 for detecting light intensity of each wavelength range dispersed by the diffraction grating 6, a first concave mirror 8a for collecting the light dispersed by the diffraction grating 6 through the first optical path C1 and converging on to the detecting surface of the photodetector array 9, and a second concave mirror 8b for collecting the light dispersed by the diffraction grating 6 through the second optical path C2 and converging on to the detecting surface of the photodetector array 9. For the purpose of following explanation, it is assumed that a direction parallel to the optical path of the collimator lens 2 is a Z direction, a direction which is in a plane parallel to the Z direction and the direction of the light reflected by the polarizing beam splitter plate 3 come out from the collimator lens 2 and which is perpendicular to the Z direction is a Y direction, and a direction perpendicular to both of the Z direction and the Y direction is an X direction.

Figures 2A, 2B, 2C:
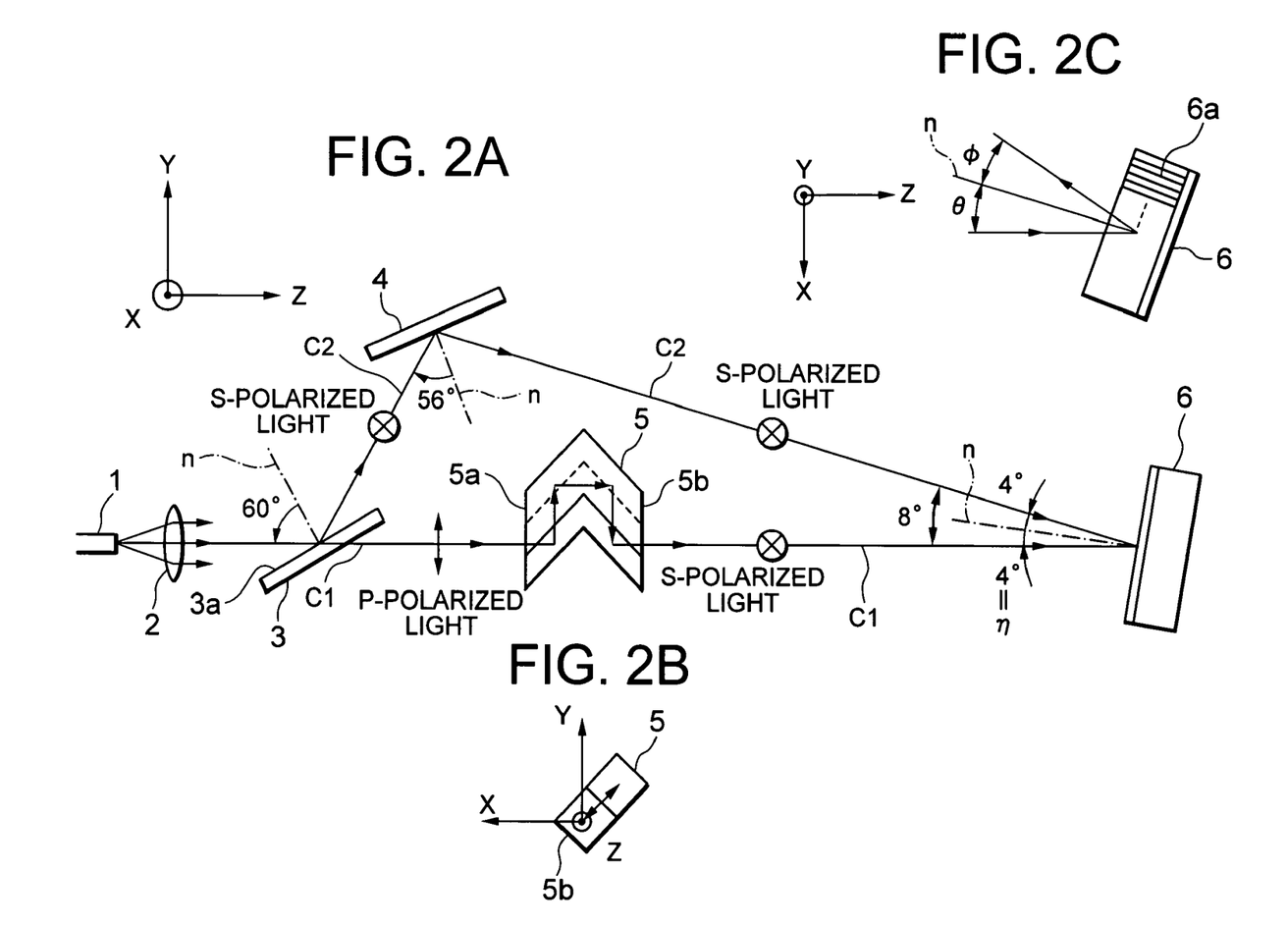
FIG. 2A is a side view showing a major portion of the spectroscope.
FIG. 2B is a graph showing a Fresnel rhomb half wave plate seen from the Z axis.
FIG. 2C is a graph showing a diffraction grating seen from the Z axis.

The polarizing beam splitter plate 3 constructed by a plane parallel glass on which a dielectric reflection coating is applied. As shown in FIG. 2A, the incident angle of the light on to the incident surface 3a is set to 60 degrees. By the way, the incident angle denotes an angle of the incident light relative to the normal n of the incident plane. A portion of the light come out from the collimator lens 2 is reflected by the polarizing beam splitter plate 3 to become S-polarized light, and proceeds along the second optical path C2 parallel to the YZ plane. The rest of the light passes through the polarizing beam splitter plate 3 to become P-polarized light, and proceeds along the first optical path C1 parallel to the optical axis. Incidentally, FIG. 2A is a graph showing a spectroscope according to the embodiment of the present invention seen from the X direction. FIG. 2B is a graph showing a Fresnel rhomb type half wave plate 5 seen from the Z direction. FIG. 2C is a graph showing the diffraction grating 6 seen from the Z direction.

The Fresnel rhomb type half wave plate 5 is a birefringent element using total internal reflection having extremely small wavelength dependency capable of being used for the light having various wavelengths. In the Fresnel rhomb type half wave plate 5, the light entered from the incident surface 5a is reflected four times in a plane, and comes out from an exit surface 5b. In the Fresnel rhomb type half wave plate 5, the incident surface 5a and the exit surface 5b are perpendicular to the z direction, and the above-described plane is disposed to make an angle of 45 degrees relative to the ZX plane as shown in FIG. 2B. With arranging the Fresnel rhomb type half wave plate 5 in this manner, the P-polarized light passing through the polarizing beam splitter plate 3 is varied polarization state thereof by ⅛ wavelength for each total internal reflection to obtain ½ wavelength totally, so that P-polarized light is converted into S-polarized light. The S-polarized light proceeds along the optical axis of the collimator lens 2, in other words, in a direction parallel to the Z direction and is incident to the diffraction grating 6.

The plane mirror 4 that deflects the second optical path C2 is disposed such that the incident angle of the S-polarized light in the second optical path C2 becomes 56 degrees. When the plane mirror 4 is disposed such that the incident angle of the S-polarized light in the second optical path C2 becomes 60 degrees, the S-polarized light reflected by the plane mirror 4 becomes parallel to the P-polarized light beam passing through the polarizing beam splitter plate 3 and parallel to the S-polarized light converted by the Fresnel rhomb type half wave plate 5 and parallel to the Z direction. On the other hand, in the embodiment of the present invention, as described above, since the plane mirror 4 is disposed such that the incident angle of the S-polarized light in the second optical path C2 becomes 56 degrees, the S-polarized light beam reflected by the plane mirror 4 and proceeding along the second optical path C2 crosses the S-polarized light proceeding along the first optical path C1 at a position separated a given distance from the plane mirror 4 with an angle of 8 degrees. The above-described diffraction grating 6 is disposed at the position where the two light beams cross. Accordingly, the incident area of the S-polarized light proceeding along the first optical path C1 and the incident area of the S-polarized light proceeding along the second optical path C2 overlap each other on the incident surface of the diffraction grating 6. Accordingly, the width in the Y direction of the diffraction grating 6, in other words, the width in the direction of grooves 6a of the diffraction grating 6 can be narrowed.

The diffraction grating 6 is disposed such that the normal n of the incident surface makes an angle of 4 degrees to the ZX plane (see FIG. 2A), and an angle of θ to the YZ plane (see FIG. 2C), and the grooves 6a extends substantially in the Y direction, to be more accurate, in the direction making an angle of 8 degrees to the Y direction. Since the diffraction grating 6 is disposed in such manner, in the YZ plane, the incident angle of the light converted from the P-polarized light to the S-polarized light proceeding along the first optical path C1 to the diffraction grating 6 is 4 degrees and the incident angle of the S-polarized light proceeding along the second optical path C2 to the diffraction grating 6 is −4 degrees.

In other words, since both of the optical paths C1 and C2 are parallel to the YZ plane, the incident angle of the S-polarized light proceeding along the first optical path C1 to the diffraction grating 6 and the incident angle of the S-polarized light proceeding along the second optical path C2 to the diffraction grating 6 are the same angle θ in the plane perpendicular to the groove 6a of the diffraction grating 6. Since the first optical path C1 makes an angle of 8 degrees to the second optical path C2 in a plane parallel to the YZ plane, the absolute values of those incident angles are the same although those incident angles are different in a plane including the groove 6a of the diffraction grating 6. By the way, as long as the absolute value of the incident angle of the S-polarized light in a plane parallel to the YZ plane is within a given tolerance range regarding the first optical path C1 and the second optical path C2, there is no problem.

When a direction of the incident light to the diffraction grating 6 is parallel to a plane perpendicular to the groove 6a of the diffraction grating 6, a direction of light to each wavelength range come out from the diffraction grating 6 generally becomes parallel to the plane perpendicular to the groove 6a of the diffraction grating 6. In this case, the following conditional expression (1) is satisfied:

$$\sin\theta + \sin\phi = n\lambda \tag{1}$$

where θ denotes an incident angle to the diffraction grating 6, φ denotes an exit angle, n denotes the number of grooves per unit length, and λ denotes a wavelength.

However, in the embodiment of the present invention, since the direction of the light incident to the diffraction grating 6 is inclined with respect to the plane perpendicular to the groove 6a of the diffraction grating 6, conditional expression (1) is not satisfied, but the following conditional expression (2) is satisfied:

$$(\sin\theta + \sin\phi)\cos\eta = n\lambda \tag{2}$$

where η denotes an angle of incident light beam to the plane perpendicular to the groove of the diffraction grating, in other words, an incident angle of depression.

In the embodiment of the present invention, since the incident angles of depression are ±4 degrees, cosη of conditional expression (2) becomes 0.9975≈1 and this can be substantially neglected, so that conditional expression (1) is satisfied also in the embodiment of the present invention.

However, the reason why conditional expression (1) is satisfied is that the incident surface of the diffraction grating 6 is inclined to the XY plane by 8 degrees such that the absolute value (4 degrees) of the incident angle of depression of the S-polarized light incident to the diffraction grating 6 through the first optical path C1 relative to the plane perpendicular to the groove 6a of the diffraction grating 6 and the absolute value (4 degrees) of the incident angle of depression of the S-polarized light incident to the diffraction grating 6 through the second optical path C2 relative to the plane perpendicular to the groove 6a of the diffraction grating 6 come to the same value. When the incident angle of depression of the S-polarized light incident to the diffraction grating 6 through the first optical path C1 relative to the plane perpendicular to the groove 6a of the diffraction grating 6 is made 0 degree and the incident angle of depression of the S-polarized light incident to the diffraction grating 6 through the second optical path C2 relative to the plane perpendicular to the groove 6a of the diffraction grating 6 is made −8 degrees, conditional expression (1) is satisfied regarding the S-polarized light incident to the diffraction grating 6 through the first optical path C1 since cosη becomes 1 (η=0°). However, regarding the S-polarized light incident to the diffraction grating 6 through the second optical path C2, since cosη becomes 0.990 (η=−8°), the factor cannot be neglected under certain circumstances, so that about 1% wavelength error produces between these two light beams passing through these two optical paths detected by the same detector.

As shown in FIG. 1, the light passing through the first optical path C1 dispersed by the diffraction grating 6 is converged onto the photodetector array 9 by the first concave mirror 8a, and the light passing through the second optical path C2 dispersed by the diffraction grating 6 is similarly converged onto the photodetector array 9 by the second concave mirror 8b.

Incidentally, in the technique disclosed in U.S. Pat. No. 6,498,872 B2, since an S-polarized light beam and an S-polarized light beam converted from a P-polarized light beam are led to a diffraction grating parallel with each other, the light beam of each wavelength range of the S-polarized light dispersed by the diffraction grating and the light beam of each wavelength range of the former P-polarized light dispersed by the diffraction grating become parallel with each other, so that in order to converge these two light beams onto the same range of the input surface of the photodetector array, it is necessary to dispose a large concave mirror or two small off-axis concave mirrors. The large concave mirror or off-axis concave mirrors are costly in either case.

On the other hand, in the embodiment of the present invention, although the two concave mirrors are used, since the light beam passing through the first optical path C1 dispersed by the diffraction grating 6 and the light beam passing through the second optical path C2 dispersed by the diffraction grating 6 make a given angle, in particular 8 degrees, and make a similar angle upon incident on the photodetector array, it is not necessary to make the concave mirrors off-axis, so that it becomes possible to suppress the increase in fabrication cost.

For the photodetector array 9, 32 Photomultiplier Tubes (PMT) are used. The plurality of PMTs are arranged in the direction that the plurality of grooves 6a of the diffraction grating 6 forms a line, in other words, in the direction of the dispersion. In the embodiment of the present invention, since a photodetector array 9 having a plurality of photodetectors is used as a photodetector in such manner, the light of a plurality of wavelength ranges can be detected at the same time. In the embodiment of the present invention, by rotating the diffraction grating table 7 on which the diffraction gratings 6 are placed, the incident angle θ and the exit angle φ of the light vary relative to the diffraction grating, so that the wavelength range capable of being detected by the photodetector array 9 can be varied.

As described above, in the embodiment of the present invention, since the direction of polarization of the light incident onto the diffraction grating 6 is aligned by using the polarizing beam splitter plate 3 and the Fresnel rhomb type half wave plate 5, troubles caused by polarization dependency of the diffraction grating 6 can be solved. Moreover, in the embodiment of the present invention, since each light beam separated by the polarizing beam splitter plate 3 into the optical paths C1 and C2 is incident on the same area of the input surface of the diffraction grating 6, it becomes possible to prevent the diffraction grating 6 from getting large, so that it becomes possible to suppress the increase in the size and the cost of the spectroscope.

Figure 3:
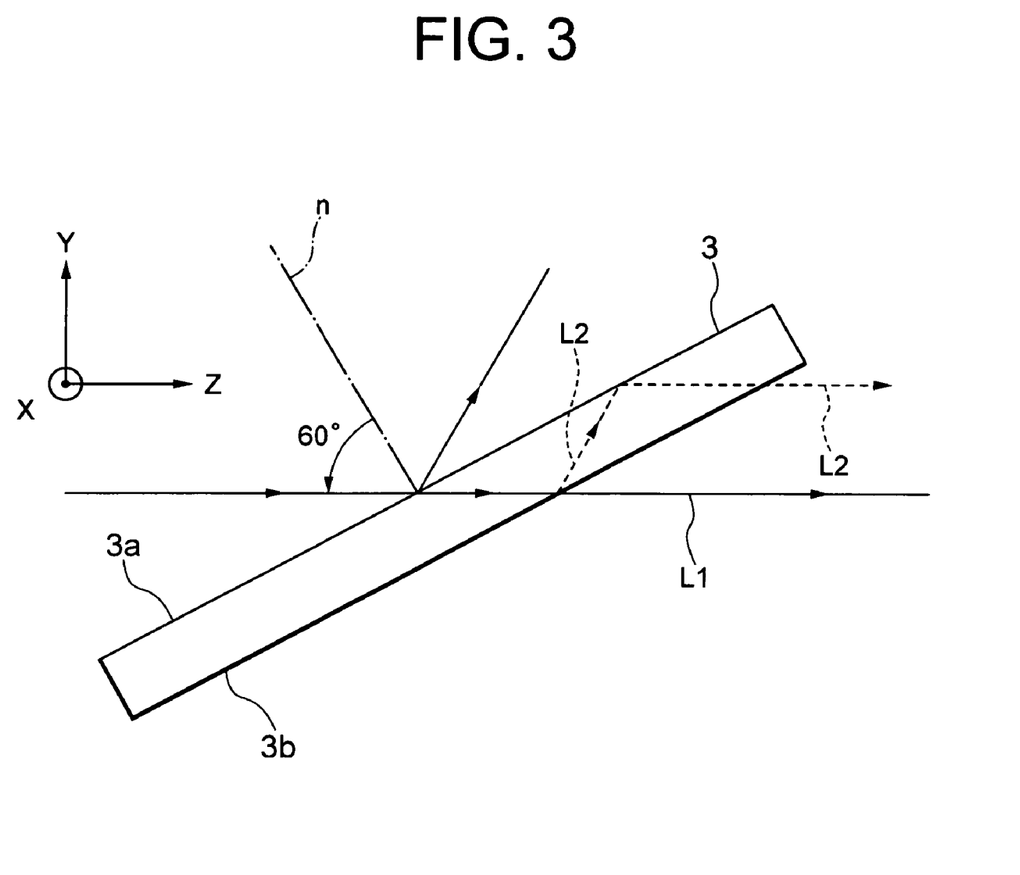
FIG. 3 is a graph explaining a polarizing beam splitter plate according to the embodiment of the present invention and optical paths passing through the plate.

In the embodiment of the present invention, the polarizing beam splitter plate 3 having a plane parallel plate shape is used as a polarization dividing element as shown in FIG. 3. A portion of light incident from the incident surface 3a of the polarizing beam splitter plate 3 is reflected by the exit surface 3b, and the light L2 after reflected by the incident surface 3a comes out from the exit surface 3b. Since the light L2 is shifted from the light L1 incident from the incident surface 3a come out from the exit surface 3b, it is possible to prevent the light L2 forming an image as a ghost on the incident surface of the photodetector array 9. Moreover, even if the light reflected from the incident surface of the photodetector array 9 is returned by reflected from the concave mirror 8a or 8b and the surface of the diffraction grating 6, the returned light is not reflected again in the direction of the photodetector array 9, so that forming a ghost image can be prevented. In particular in the embodiment of the present invention, since the incident angle to the polarizing beam splitter plate 3 is made to be 60 degrees larger than 45 degrees, the above-described amount of shift becomes large, so that it becomes possible to effectively prevent a ghost image.

Figure 4:
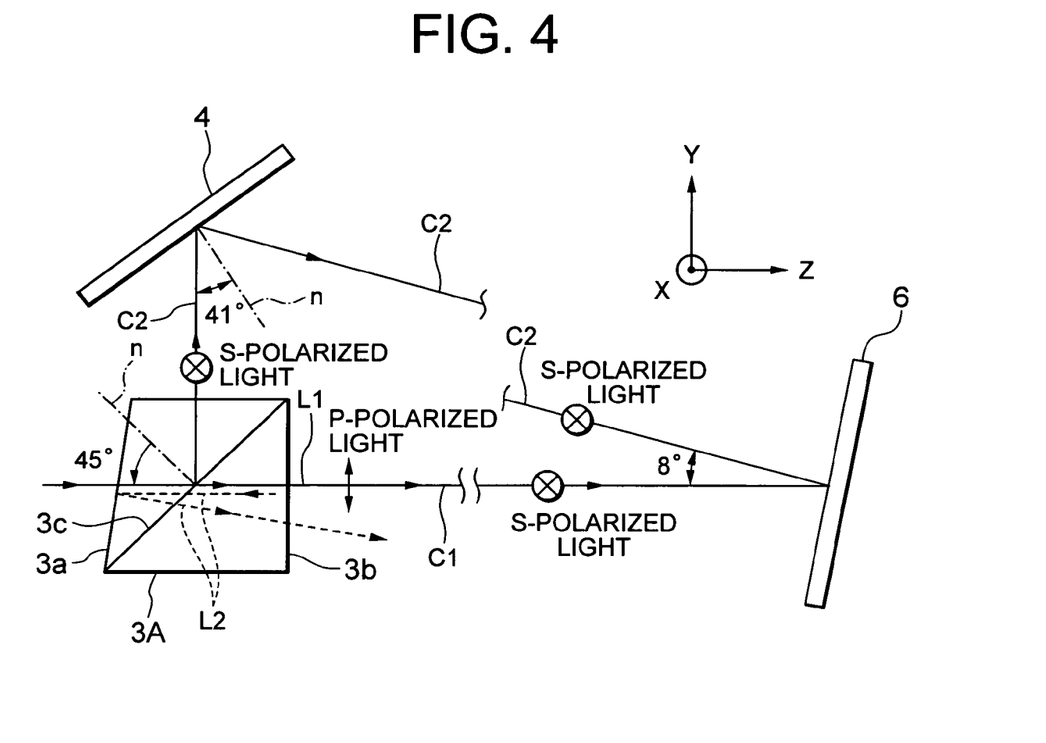
FIG. 4 is a side view of the main portion of a spectroscope as a variation according to an embodiment of the present invention.

As for preventing a ghost image other than the way that the polarizing beam splitter plate 3 having a plane parallel plate shape is largely inclined, there is a way that a polarizing beam splitter cube 3A is used as shown in FIG. 4. Specifically, a cube that has a reflecting surface 3c making an angle of 45 degrees to an exit surface 3b and an incident surface 3a is slightly inclined with respect to the exit surface 3b is used. In this case, when the polarizing beam splitter cube 3A is arranged such that the incident angle to the reflecting surface 3c becomes 45 degrees, and a plane mirror 4 for changing the direction of the light reflected from the reflecting surface 3c is arranged such that the incident angle of the light reflected from the polarizing beam splitter cube 3A becomes 41 degrees, the light directly passing through the polarizing beam splitter cube 3A and the light reflected from the plane mirror 4 make an angle of 8 degrees as same as the former embodiment. Since the incident surface 3a is inclined with respect to the exit surface 3b in this manner, even if a portion of light incident from the incident surface 3a of the polarizing beam splitter cube 3A is reflected by the exit surface 3b, and the light L2 after reflected by the incident surface 3a comes out from the exit surface 3b, the light L2 makes a certain angle to the light L1 incident from the incident surface 3a passing through the exit surface 3b, so that it becomes possible to prevent from forming a ghost image on the incident surface of the photodetector array 9. Moreover, even if the light reflected from the incident surface of the photodetector array 9 is returned by reflected from the concave mirror 8a or 8b and the surface of the diffraction grating 6, the returned light is not reflected again in the direction of the photodetector array 9, so that forming a ghost image can be prevented.

In the above-described embodiments, although the plane mirror 4 is arranged in the second optical path C2 such that the light beams proceeding through the respective optical paths C1 and C2 are incident on the same range of the diffraction grating 6, it is needless to say that the plane mirror 4 may be arranged in the first optical path C1. In the above-described embodiments, although the light dispersed by the diffraction grating 6 is collected by the concave mirrors 8a and 8b and detected by the photodetector array 9, an exit slit for outputting the light having a specific wavelength range may be arranged instead of the photodetector array 9. In the above-described embodiments, although the incident angle of the light proceeding through the first optical path C1 to the diffraction grating 6 and the incident angle of the light proceeding through the second optical path C2 to the diffraction grating 6 are substantially the same in the plane perpendicular to the grooves 6a of the diffraction grating 6 and different in the plane including the groove 6a, it may be possible to construct such that these angles are different in the plane perpendicular to the grooves 6a of the diffraction grating 6 and substantially the same in the plane including the groove 6a. In other words, it may be possible to construct such that horizontal and vertical relation of the diffraction grating 6 according to the embodiment of the present invention becomes reverse. However, since difference in secondary dispersion can be avoided in the diffraction grating 6, the configuration of the diffraction grating 6 according to the present embodiment of the present invention is better.

Figure 5:
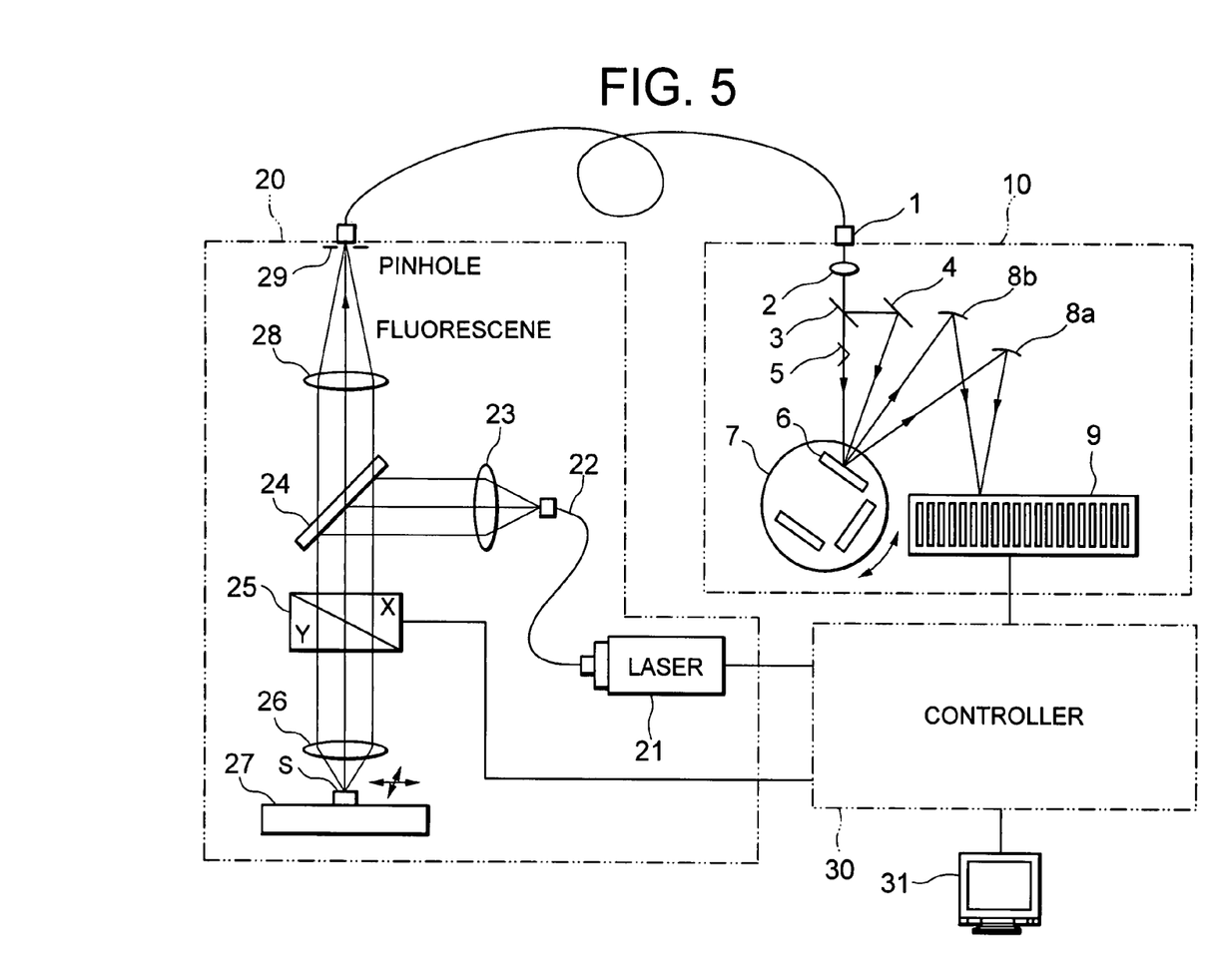
FIG. 5 is a graph-showing a construction of a microspectroscope according to an embodiment of the present invention.

Then an embodiment of a microspectroscope using the above-described spectroscope is explained with reference to FIG. 5.

The microspectroscope according to an embodiment of the present invention includes a confocal microscope 20, a spectroscope 10 for dispersing the light output from the confocal microscope 20 and detecting light intensity of each wavelength range, and controller 30 for processing image data output from the spectroscope 10 and making a display 31 show the data together with controlling movement of the confocal microscope 20.

The confocal microscope 20 includes a laser light source 21, an optical fiber 22 for leading the light output from the laser light source 21 to a given position, a collimator lens 23 for collimating the laser light output from the laser light source 21, a dichroic mirror 24 for receiving the laser light collimated by the collimator lens 23, a galvano-mirror 25 for two-dimensionally scanning the laser light reflected from the dichroic mirror 24 on the sample S, an objective lens 26 for converging the light from the galvano-mirror 25 onto an observing surface of the sample S, a pinhole plate 29 disposed in a position optically conjugate with the observing surface of the sample S, and a collecting lens 28 for collecting the laser light reflected from the observing surface of the sample S and converging on to the pinhole of the pinhole plate 29.

An illumination optical system of the confocal microscope 20 is composed of the laser light source 21, the optical fiber 22, the collimator lens 23, the dichroic mirror 24, the galvano-mirror 25, and the objective lens 26. An observation optical system of the confocal microscope 20 is composed of the objective lens 26, the galvano-mirror 25, the dichroic mirror 24, and the collecting lens 28. Accordingly, the illumination optical system and the observation optical system commonly own the objective lens 26, the galvano-mirror 25, and the dichroic mirror 24.

The light passing through the pinhole of the confocal microscope 20 is led to the spectroscope 10 through the input fiber 1 of the spectroscope 10. In the spectroscope 10, the light from the confocal microscope 20 is dispersed by the diffraction grating 6 and the light intensity of each wavelength range is detected by the photodetector array 9.

The photodetector array 9 sends the detected data to the controller 30. The controller 30 carries out a given image processing to the data and sends it to the display 31 as an image data.

In the embodiment of the present invention, although the light passing through the pinhole of the confocal microscope 20 is led to the spectroscope 10, it may be possible that a slit for working as a pinhole and disposed in the position of the pinhole is formed, the spectroscope 10 is connected directly on the slit, and the slit is made to be an input port of the spectroscope 10. In other words, it may be possible that the input portion of the spectroscope 10 is used as the pinhole of the confocal microscope 20. As described above, when the spectroscope 10 is connected directly on the confocal microscope 20 in this manner, the merit capable of miniaturizing the spectroscope 10 becomes crucially important.

As described above, the present invention makes it possible to provide a spectroscope capable of substantially superposing two light beams passing through respective optical paths separated by a polarization dividing element on the surface of a spectroscopic element by means of a beam deflector to prevent the size of the spectroscopic element from getting large resulting in suppressing the dimension and the cost of the microspectroscope.

Additional advantages and modification will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A spectroscope comprising:
    an input portion;
    a spectroscopic element that disperses light come out from the input portion;
    an exit portion that exits the light dispersed by the spectroscopic element, or a detector that detects the light dispersed by the spectroscopic element;
    a polarization dividing element that divides the light from the input portion into a first optical path and a second optical path and gives each light of each optical path different direction of polarization with each other;
    a polarization rotator that is disposed in the first optical path and arranges the direction of polarization of the light in the first optical path into the direction of polarization of the light in the second optical path; and
    a beam deflector that is disposed in either one optical path of the first optical path and the second optical path and deflects the one optical path such that at least a portion of an area where the light proceeding through the one optical path is incident on the spectroscopic element and an area where the light proceeding through the other optical path is incident on the spectroscopic element overlap each other.

2. The spectroscope according to claim 1, wherein the polarization dividing element is a polarizing beam splitter plate having a plane parallel plate shape.

3. The spectroscope according to claim 1, wherein the polarization dividing element is a polarizing beam splitter cube having an incident surface and an exit surface and the incident surface of the polarizing beam splitter cube is inclined with respect to the exit surface.

4. The spectroscope according to claim 3, wherein the incident surface of the polarizing beam splitter cube is not perpendicular to the incident light.

5. The spectroscope according to claim 1, wherein the polarization rotator is a Fresnel rhomb half wave plate.

6. The spectroscope according to claim 1, further comprising a superposition optical element that superposes at least a portion of an area where the light proceeding through the other optical path and being dispersed by the spectroscopic element is incident on the exit portion or the detector upon an area where the light proceeding through the one optical path and being dispersed by the spectroscopic element is incident on the exit portion or the detector.

7. A microspectroscope comprising:
    a confocal microscope; and
    the spectroscope according to claim 6;
    the confocal microscope including;
        a laser light source;
        a converging optical system that converges the light from the laser light source onto an observing surface;
        a pinhole member on which a pinhole, which is optically conjugate with the observing surface, is formed; and
        an optical system capable of converging the light reflected from the observing surface onto the pinhole;
    the spectroscope dispersing the light passing through the pinhole of the confocal microscope.

8. The spectroscope according to claim 1, wherein the spectroscopic element is a diffraction grating on which a plurality of grooves are formed parallel with each other and an incident angle of the light proceeding through the one optical path incident on the diffraction grating and an incident angle of the light proceeding through the other optical path incident on the diffraction grating are substantially the same angle in a plane perpendicular to the direction of the groove and different in a plane including the groove.

9. The spectroscope according to claim 8, wherein the incident angle of the light proceeding through the one optical path incident on the diffraction grating and the incident angle of the light proceeding through the other optical path incident on the diffraction grating have the same absolute value.

10. The spectroscope according to claim 9, wherein the polarization dividing element is a polarizing beam splitter plate having a plane parallel plate shape.

11. The spectroscope according to claim 9, wherein the polarization dividing element is a polarizing beam splitter cube having an incident surface and an exit surface and the incident surface of the polarizing beam splitter cube is inclined with respect to the exit surface, and not perpendicular to the incident light.

12. The spectroscope according to claim 9, wherein the polarization rotator is a Fresnel rhomb half wave plate.

13. The spectroscope according to claim 9, further comprising a superposition optical element that superposes at least a portion of an area where the light proceeding through the other optical path and being dispersed by the spectroscopic element is incident on the exit portion or the detector upon an area where the light proceeding through the one optical path and being dispersed by the spectroscopic element is incident on the exit portion or the detector.

14. A microspectroscope comprising:
    a confocal microscope; and
    the spectroscope according to claim 9;
    the confocal microscope including;
        a laser light source;

a converging optical system that converges the light from the laser light source onto an observing surface;

a pinhole member on which a pinhole, which is optically conjugate with the observing surface, is formed; and an optical system capable of converging the light reflected from the observing surface onto the pinhole;

the spectroscope dispersing the light passing through the pinhole of the confocal microscope.

15. A microspectroscope comprising:
a confocal microscope; and
the spectroscope according to claim 1;
the confocal microscope including;

a laser light source;

a converging optical system that converges the light from the laser light source onto an observing surface;

a pinhole member on which a pinhole, which is optically conjugate with the observing surface, is formed; and an optical system capable of converging the light reflected from the observing surface onto the pinhole;

the spectroscope dispersing the light passing through the pinhole of the confocal microscope.

* * * * *